(12) United States Patent
McLaughlin et al.

(10) Patent No.: US 8,591,585 B2
(45) Date of Patent: Nov. 26, 2013

(54) EXPANDABLE VERTEBRAL IMPLANT

(75) Inventors: Colm McLaughlin, Philadelphia, PA (US); Jason Gray, East Greenville, PA (US); James Himmelberger, Souderton, PA (US); Thomas Shinn, Collegeville, PA (US); Mark Adams, Downington, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 13/333,227

(22) Filed: Dec. 21, 2011

(65) Prior Publication Data

US 2012/0130493 A1    May 24, 2012

Related U.S. Application Data

(63) Continuation-in-part of application No. 12/758,529, filed on Apr. 12, 2010, now Pat. No. 8,282,683.

(51) Int. Cl.
*A61F 2/44* (2006.01)

(52) U.S. Cl.
USPC .................................................. 623/17.15

(58) Field of Classification Search
USPC .................... 623/17.11–17.16; 403/321–330
See application file for complete search history.

(56) References Cited

U.S. PATENT DOCUMENTS

| 6,344,057 | B1 | 2/2002 | Rabbe | |
|---|---|---|---|---|
| 7,059,420 | B1 * | 6/2006 | Wei | 172/375 |
| 8,197,546 | B2 * | 6/2012 | Doubler et al. | 623/17.15 |
| 2002/0117412 | A1 * | 8/2002 | Rabiner et al. | 206/363 |
| 2003/0132131 | A1 * | 7/2003 | Rabiner et al. | 206/438 |
| 2003/0176925 | A1 * | 9/2003 | Paponneau | 623/17.16 |
| 2006/0241770 | A1 | 10/2006 | Rhoda | |
| 2007/0255410 | A1 * | 11/2007 | Dickson et al. | 623/17.11 |
| 2008/0046082 | A1 * | 2/2008 | Lee | 623/17.16 |
| 2009/0138089 | A1 * | 5/2009 | Doubler et al. | 623/17.16 |
| 2009/0164017 | A1 | 6/2009 | Sommerich | |
| 2010/0179655 | A1 * | 7/2010 | Hansell et al. | 623/17.11 |
| 2010/0274357 | A1 | 10/2010 | Miller | |
| 2010/0286787 | A1 | 11/2010 | Villiers | |
| 2011/0251691 | A1 * | 10/2011 | McLaughlin et al. | 623/17.16 |
| 2011/0251692 | A1 | 10/2011 | McLaughlin | |

* cited by examiner

*Primary Examiner* — Ellen C Hammond
*Assistant Examiner* — Jacqueline Johanas

(57) ABSTRACT

The present invention relates to an expandable implant for engagement between vertebrae generally comprising an inner member, outer member, and gear member positioned coaxial with respect to each other such that the inner and outer members are moveable relative to each other along an axis. The gear member is axially fixed to the outer member and freely rotatable with respect to the outer member and the gear member threadedly engages a threaded portion of the inner member to translate inner member along the axis. The implant is configured to engage the vertebrae in a predetermined alignment and the gear member includes gear teeth exposed to the exterior and configured to be accessible by a tool member at a plurality of angular positions around the perimeter of the implant device.

18 Claims, 16 Drawing Sheets

EXPANDABLE VERTEBRAL IMPLANT

CROSS-REFERENCE TO RELATED APPLICATIONS

This application is a continuation-in-part of U.S. patent application Ser. No. 12/758,529 entitled "Expandable Vertebral Implant," filed on Apr. 12, 2010 now U.S. Pat. No. 8,282,683, the entire disclosure of which is incorporated herein by reference.

FIELD OF THE INVENTION

The present invention relates to a device to support the spine after removal of at least a part of a vertebra.

BACKGROUND OF THE INVENTION

When a vertebra is damaged or diseased, surgery may be used to replace the vertebra or a portion thereof with a prosthetic device to restore spinal column support. For example, vertebral body replacement is commonly required in the treatment of vertebral fracture, tumor, or infection.

In recent years, several artificial materials and implants have been developed to replace the vertebral body, such as, for example, titanium cages, ceramic, ceramic/glass, plastic or PEEK, and carbon fiber spacers. Recently, various expandable prosthetics or expandable cages have been developed and used for vertebral body replacement. The expandable prosthetic devices are generally adjustable to the size of the cavity created by a corpectomy procedure and typically are at least partially hollow to accommodate bone cement or bone fragments to facilitate fusion in vivo. Some expandable implants may be adjusted prior to insertion into the cavity, while others may be adjusted in situ. Two advantages of the vertebral body replacement using an expandable prosthetic device that is adjustable in situ is that it is easy to place or insert and it permits an optimal, tight fit and correction of the deformity by in vivo expansion of the device. Some other advantages offered by an expandable prosthetic device are that they can facilitate distraction across the resected vertebral defect for correction of the deformity, and allow immediate load bearing after corpectomy.

Instrumentation and specialized tools for insertion of a vertebral implant is one important design parameter to consider when designing a vertebral implant. Spinal surgery procedures can present several challenges because of the small clearances around the prosthetic when it is being inserted into position. Another important design consideration includes the ability of the device to accommodate various surgical approaches for insertion of the vertebral implant.

SUMMARY OF THE INVENTION

The present invention relates to an expandable prosthetic implant device for engagement between vertebrae generally comprising an inner member, outer member, and gear member positioned coaxial with respect to each other such that the inner and outer members are moveable relative to each other along an axis. The inner member has a hollow interior portion and a threaded external portion and includes a first end portion configured to engage an endplate which is capable of engaging a first vertebral body. The outer member has a hollow interior portion configured to receive the inner member and includes a second end portion configured to engage an endplate which is capable of engaging a second vertebral body. The gear member is axially fixed to the outer member and freely rotatable with respect to the outer member and the gear member threadedly engages the threaded portion of the inner member.

The implant is configured to engage the vertebrae such that first and second end portions are oriented in a predetermined alignment with respect to the first and second vertebral bodies. The gear member includes teeth extending around the perimeter of the gear member and the teeth are exposed to the exterior and configured to be accessible by a tool member.

BRIEF DESCRIPTION OF THE DRAWINGS

The present invention will be more readily understood with reference to the embodiments thereof illustrated in the attached drawing figures, in which.

Throughout the drawing figures, it should be understood that like numerals refer to like features and structures.

DETAILED DESCRIPTION OF THE PREFERRED EMBODIMENTS

Figure 1:
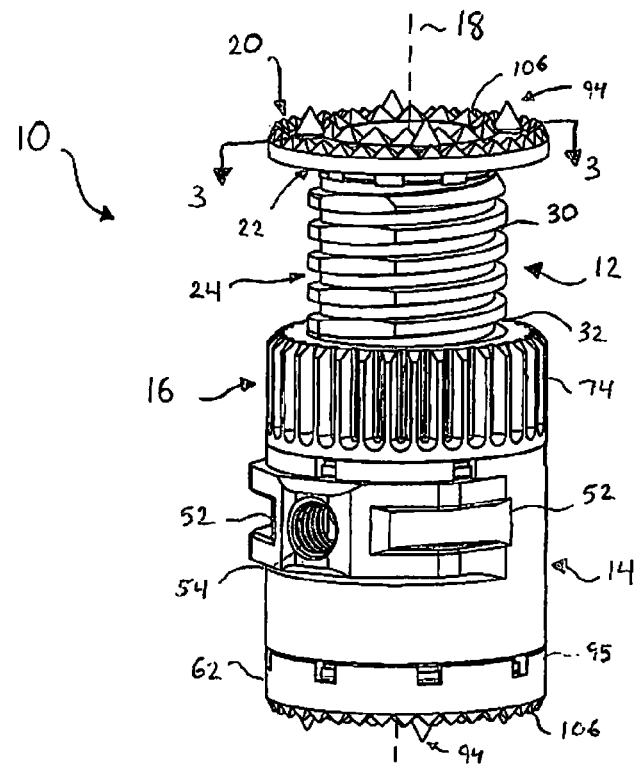
FIG. 1 is a perspective view of an implant in accordance with an embodiment of the present invention.

The preferred embodiments of the invention will now be described with reference to the attached drawing figures. The following detailed description of the invention is not intended to be illustrative of all embodiments. In describing preferred embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

Referring to FIGS. 1-6, a preferred embodiment of an expandable vertebral implant 10 is shown. The implant 10 preferably comprises an inner member 12 which may be telescopingly received within an outer member 14. The implant 10 further comprises a gear member 16 generally configured to effect translation of the inner member 12 with respect to the outer member 14 thereby allowing for expansion and contraction of the implant 10. The inner member 12, the outer member 14, and the gear member 16 are preferably centered along a longitudinal axis 18 and define a hollow interior portion which may be filled with bone material, bone growth factors, bone morphogenic proteins, or other materials for encouraging bone growth, blood vessel growth or growth of other tissue through the many apertures in the device. In one preferred embodiment, members 12, 14, and 16 are made of a polyether ether ketone (PEEK) plastic material. There are several known advantages of PEEK plastic material including being radiolucent, having a mechanical strength that is close to bone, and may be more easily sterilized than other plastics. In alternate preferred embodiments, the members 12, 14, and 16 may be made of a biologically inert metal alloys, such as titanium, or other suitable materials.

Referring to FIGS. 1-5, the inner member 12 has a generally cylindrical body 24 with a distal end 22 and a proximal end 36. In a preferred embodiment, the body 24 of the inner member 12 comprises an inner surface 28 and an outer surface 30 and generally defines a hollow interior portion 23 extending axially therethrough. At least part of the outer surface 30 preferably includes external threads 32. Located proximate to the distal end 22 of the body 24 are a plurality of tabs 38 which assist in connecting and positionally locating an endplate 20. In a preferred embodiment, the body 24 is configured and dimensioned to be cooperatively received within outer member 14.

Figure 5:
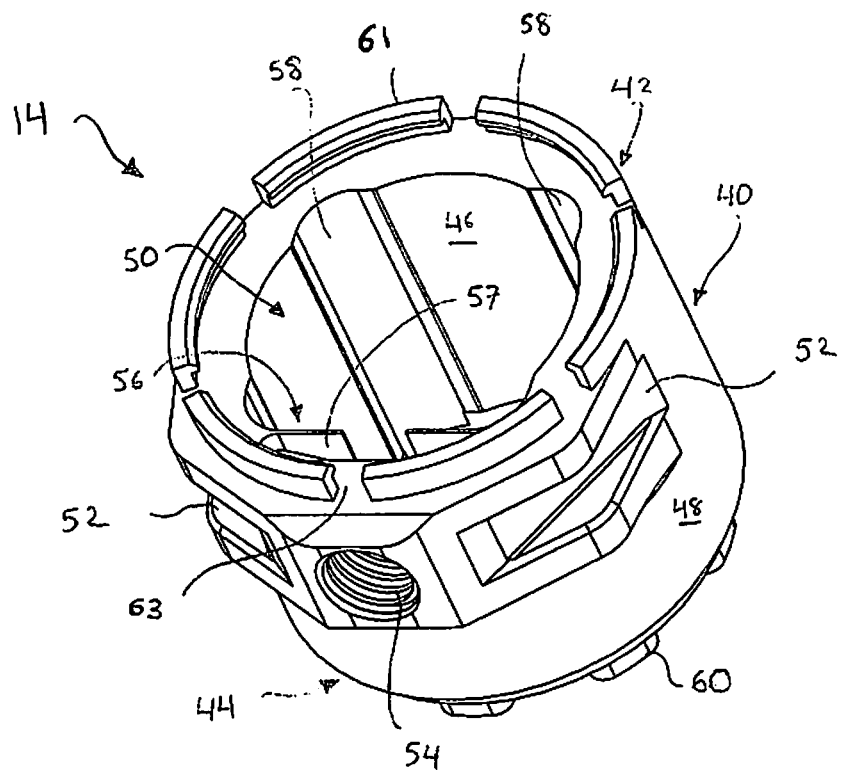
FIG. 5 is perspective view of an embodiment of an outer member of the implant of FIG. 1.

The outer member 14 has a generally cylindrical body 40 with a distal end 42 and a proximal end 44. In a preferred embodiment, the body 40 of the outer member 14 comprises an inner surface 46 and an outer surface 48 and generally defines a hollow interior portion 50 extending axially therethrough. The outer surface 48 preferably has at least one slot 52 and an opening 54 configured and dimensioned to receive a portion of an implantation tool. In a preferred embodiment, the opening 54 extends from the outer surface 48 to the hollow interior portion 50 and at least a portion of the opening 54 is threaded. As best seen in FIG. 5, the inner surface 46 includes a channel 57 for receiving a locking member (discussed below). Located proximate to the proximal end 44 of the outer member 14 are a plurality of tabs 60 which assist in connecting and positionally locating an endplate 62. In a preferred embodiment, a lip 61 is formed around the exterior of the distal end 42 of body 40 and is configured to cooperatively fit with a portion of the gear member 16. A plurality of relief spaces or slots 63 are radially spaced around lip 61 to facilitate a snapping engagement of the lip 61 with the gear member 16. In this regard, slots 63 allow the lip 61 to deform slightly and contract in the radial direction to accommodate gear member 16 to snap on to lip 61. In a preferred embodiment, the interior portion 50 of body 44 is configured and dimensioned to cooperatively receive body 24 of inner member 12 within outer member 14. In this regard, the dimensions of interior portion 50 of body 44 are greater than dimensions of body 24 of inner member 12.

As best seen in FIGS. 2-5, in a preferred embodiment of a prosthetic device 10, the body 24 of the inner member 12 includes a flattened portion 34 which extends at least in part from the distal end 22 to the proximal end 36 and includes a base member 37 having at least one lobe 39 located proximate to the distal end 36 of the body 24. Focusing on FIG. 5, the body 40 of the outer member 14 includes a flattened area 56 and at least one depression 58 on the inner surface 46. When the inner member 12 is assembled within the outer member 14, the flattened area 56 of the outer member 14 cooperatively aligns with the flattened portion 34 of the inner member 12 and the at least one depression 58 of outer member 14 receives the at least one lobe 39 of the inner member 12. The flattened portion 34 and the flattened area 56 along with the lobes 39 and the depressions 58 cooperate to allow the inner member 12 to linearly move with respect to the outer member 14 but prevent the inner member 12 from rotating with respect to the outer member 14. In addition, the base member 37 serves as a stop preventing the inner member 12 from rotating to a point of disengagement from outer member 14.

Figure 6:
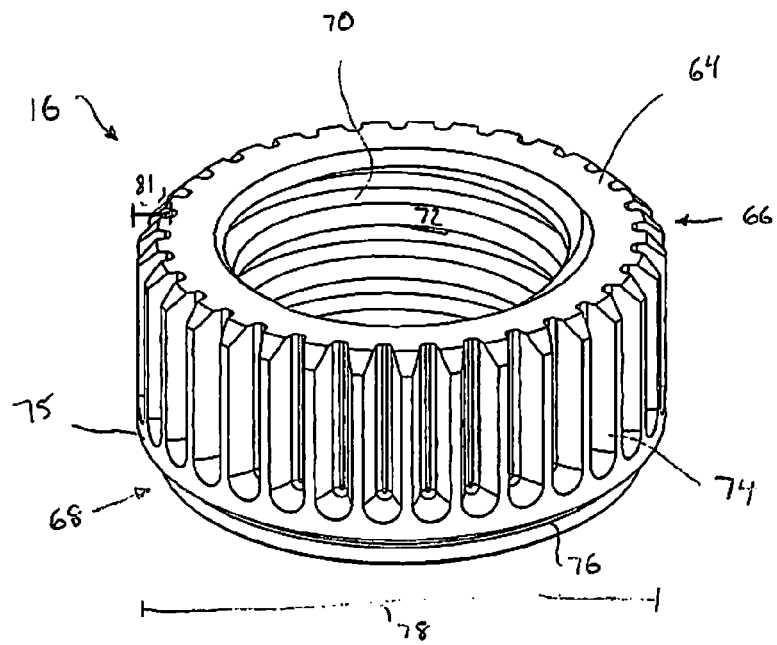
FIG. 6 is an elevated perspective view of one embodiment of a gear member of the implant of FIG. 1.
Figure 7:
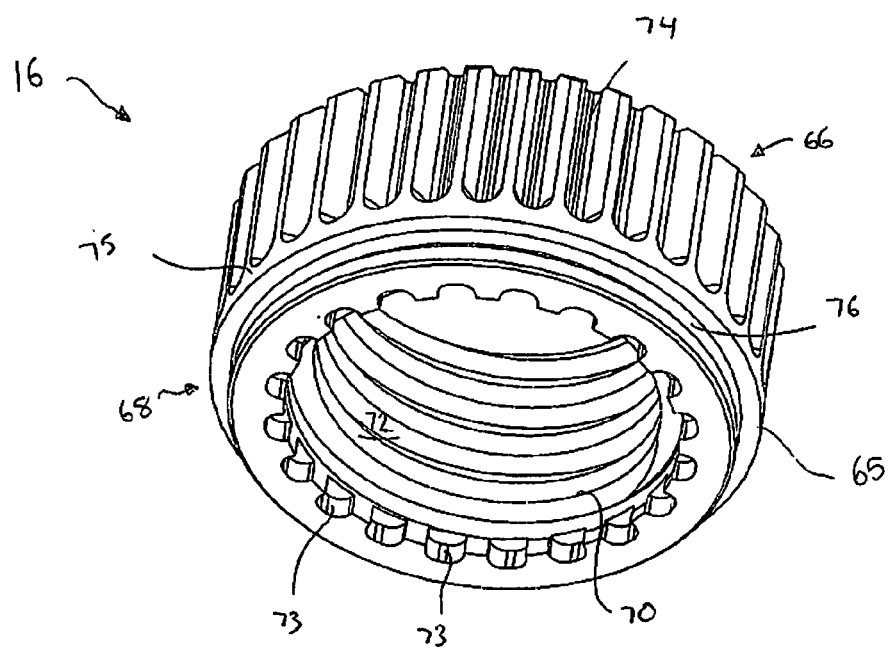
FIG. 7 is a bottom perspective view of the gear member of FIG. 6.

Referring now to FIGS. 6-7, a gear member 16 comprises a generally hollow body 64 extending from a distal end 66 to a proximal end 68 with a helical thread 70 along at least part of an inner wall 72 and an array of gear teeth 74 along a portion of the exterior wall 75. The gear member 16 is generally configured to rotatably connect to the distal end 42 of the outer member 14 and the internal helical thread 70 is configured to engage the external threads 32 of the inner member 12 to cause translation of the inner member 12 with respect to the outer member 14. In a preferred embodiment, the gear member 16 includes a cylindrical cutout feature 76 extending around the inner wall 654 to cooperatively receive the lip 54 of the outer member 14. In this regard, the gear member 16 may rotate freely with respect to the outer member 14 while being retained from longitudinal and lateral movement. In a preferred embodiment, the gear member 16 also includes a series of cutouts 73 located proximate to the proximal end 68 for engaging a portion of a locking member.

With continued reference to FIGS. 6-7, the gear teeth 74 extend substantially from the proximal end 68 to the distal end 66 and extend around the entire periphery of at least a portion of the exterior wall 75. The outer-most external diameter 78 of the gear member 16 is sized to be the same as or slightly smaller than the smallest outer diameter of the endplates 20, 62 and the outer member 14. In this regard, when the implant 10 is viewed from the end in a plane perpendicular to the longitudinal axis 18, the gear member 16 does not protrude radially outward from beyond the perimeter of the endplates 20, 62.

As shown in FIG. 7, in a preferred embodiment, the gear teeth 74 extend a width 81 in a generally radial direction and generally extend radially outward to the outer diameter of the gear member 16. In this regard, the teeth 74 may be designed to have a width 81 to accommodate the expected gear forces given the particular gear ratio, types of material used, and desired overall diameter of prosthetic device 10. One skilled in the art will appreciate that the larger the outer diameter to which the teeth 74 radially extend, the larger the teeth 74 may be designed while still maintaining the same gear ratio. In this regard, when the teeth 74 are made larger, they generally have a better mechanical strength. Also, the ability to design larger, wider, and stronger teeth 74 is advantageous for embodiments where the implant 10 is made of PEEK, other plastic, or other non-metallic materials that may have less mechanical strength than, for instance, titanium.

Furthermore, as described in one embodiment, because the outer-most diameter of the gear member 16 may be as large as the outer diameter of the endplates 20, 62, and the teeth 74 extend radially to the outer-most diameter of the gear member 16, a larger inner diameter of the gear member 16 may be manufactured without compromising mechanical gear strength. As a result, a larger overall inner diameter of the implant 10 may be accommodated which allows the packing of more bone material therein and facilitates bone fusion once the implant 10 is implanted.

Figure 3:
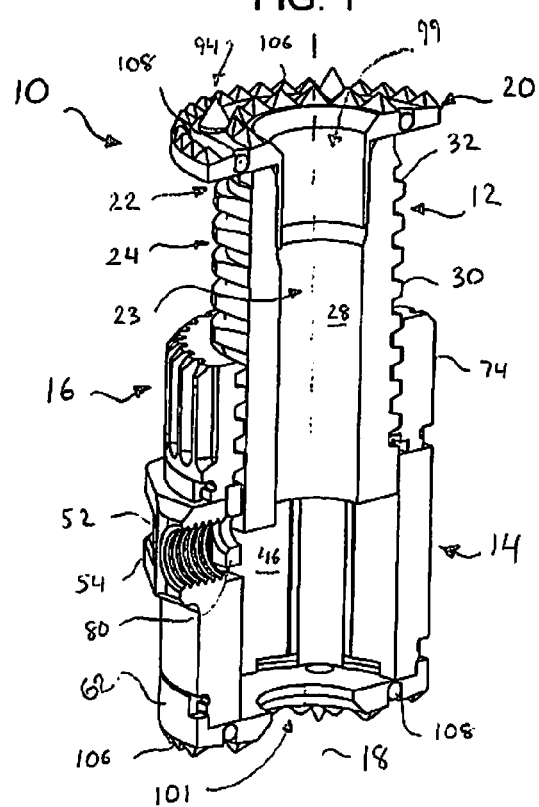
FIG. 3 is a cross-sectional view of the implant of FIG. 1 taken along line 3-3 of FIG. 1.
Figure 2:
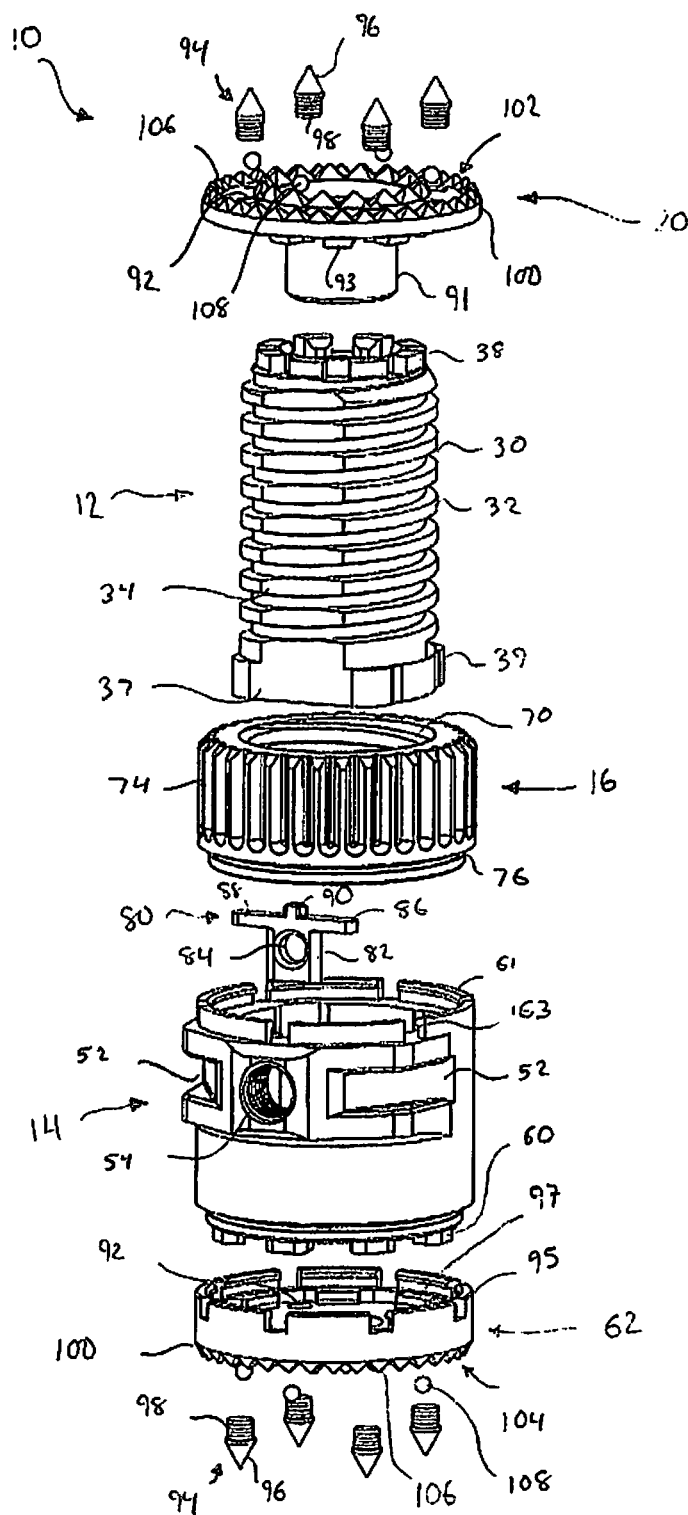
FIG. 2 is an exploded view of the implant of FIG. 1.
Figure 4:
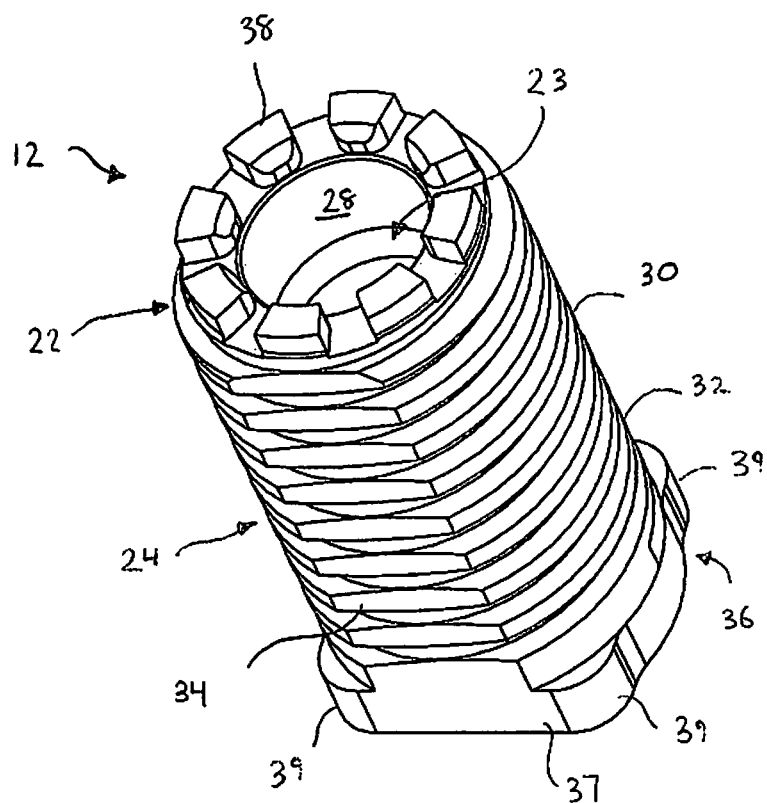
FIG. 4 is perspective view of an embodiment of an inner member of the implant of FIG. 1.

As seen in FIGS. 1-3, in a preferred embodiment, the teeth 74 are exposed to the exterior of prosthetic device 10. Because the teeth 74 are exposed around the periphery, little to no material is needed to cover up the exposed teeth, which generally makes the implant 10 lighter and easier to manufacture than prior art devices that require covering the gear teeth. In addition, the gear member 16 is more easily visible by a surgeon and more readily accessible by a rotation tool than devices that hide or cover gear teeth.

Referring to FIGS. 2, 5, and 7, in a preferred embodiment, the implant 10 also includes a locking member 80. The locking member 80 may be provided to substantially restrict all relative movement between inner member 12 and outer member 14, when, for example, the desired expansion of the prosthetic device 10 has been obtained. The locking member 80 has a body portion 82 with a through-hole 84. In a preferred embodiment, the body portion 82 has at least one, but preferably two, outwardly extending, flexible arms 86, 88 and at least one engagement member 90. In other preferred embodiments, instead of flexible arms 86, 88, it is contemplated that the locking member 80 may include an alternate biasing member, such as a leaf spring. The locking member 80 is configured and dimensioned to be received in the channel 57 of the outer member 14 in such a manner that the arms 86,88 rest against a shelf portion in the channel 57 and the through-hole 84 partially aligns with opening 54. The engagement member 90 preferably protrudes upwardly and is configured and dimensioned to engage the cutouts 73 of the gear member 16 to prevent the gear member 16 from rotating.

Referring now to FIGS. 1-3, in a preferred embodiment, the endplates 20, 62 are shown wherein the endplate 20 connects to the inner member 12 and endplate 62 connects to the outer member 14. In a preferred embodiment, endplate 20 includes an extension portion 91 which is received in the interior portion 23 of inner member 12, for example, in an interference or snap fit and includes a plurality of tabs 93 which interdigitate with tabs 38 to connect and position endplate 20 with respect to the inner member 12. Endplate 62 includes an extension portion 95 which engages the proximal end 44 of the outer member 14, for example, in an interference or snap fit and includes a plurality of tabs 97 which interdigitate with tabs 60 to connect and position endplate 62 with respect to the outer member 14. The endplates 20, 62 also preferably include hollow interior portions 99, 101 which are in fluid communication with the hollow interior portions 23, 50 of inner member 12 and outer member 14, respectively.

In a preferred embodiment, each endplate 20, 62 is generally annular in shape when viewed from the end or perpendicular to the longitudinal axis 18. It is, however, contemplated that the endplates 20, 62 can be other shapes including oblong, elliptical, kidney bean, polygonal, or geometric. Preferably, the endplates 20, 62 are designed to resemble or mimic the footprint of the vertebral body to which the endplates will engage. In this regard, endplates 20, 62 are configured to engage portions of the vertebrae in a predetermined orientation to maximize contact of the superior surface of the endplates 20, 62 with bone.

The dimensions of endplates 20, 62 can be varied to accommodate a patient's anatomy. In some embodiments, the endplates 20, 62 have a wedge-shaped profile to accommodate the natural curvature of the spine. In anatomical terms, the natural curvature of the lumbar spine is referred to as lordosis. When implant 10 is to be used in the lumbar region, the angle formed by the wedge should be approximately between 3.5 degrees and 16 degrees so that the wedge shape is a lordotic shape which mimics the anatomy of the lumbar spine. In alternate embodiments, the wedge shape profile may result from a gradual increase in height from an anterior side to a posterior side to mimic the natural curvature, kyphosis, in other regions of the spine. Thus, in other embodiments, the angle may be between about −4 degrees and −16 degrees.

As shown in FIGS. 1-3, in a preferred embodiment, the endplates 20, 62 include a plurality of mounting holes 92 spaced around the perimeter of each endplate 20, 62 for receiving insertable bone engaging members 94. In one embodiment, bone engaging members 94, comprise conical spikes 96 each having a cylindrical base portion 98 configured to fit within holes 92, for instance, by press-fit or by threaded engagement. In alternate embodiments, differently shaped bone engaging members 94 may be used, or in other embodiments no bone engaging members may be used. Referring again to FIG. 2, according to one embodiment, endplates 20, 62 have chamfered edges 100 around the perimeter to facilitate insertion and/or accommodate the shape of the vertebral bodies which they engage. The superior or bone engaging surfaces 102, 104 of endplates 20, 62 may also include numerous types of texturing to provide better initial stability and/or grasping contact between the end plate and the respective vertebrae. In a preferred embodiment, the texturing is a plurality of teeth 106. In preferred embodiments where the implant 10 is manufactured from PEEK or other plastic materials, the endplates 20, 62 may also include radio-opaque material, such as tantalum markers 108, which aid in providing location markers in radiographic images.

In preferred embodiments, the length, diameter, and shape of prosthetic device 10 may vary to accommodate different applications, different procedures, implantation into different regions of the spine, or size of vertebral body or bodies being replaced or repaired. For example, implant 10 may be expandable to a longer distance to replace multiple vertebral bodies. Also endplates 20, 62 can be sized and shaped as well as positioned to accommodate different procedures and approached to the spine. For example, endplates 20, 62 may be made smaller for smaller statured patients or for smaller regions of the cervical spine. In addition, it is not required that endplates 20, 62 be shaped and sized identically and in alternate embodiments they can be shaped or sized differently than each other and/or include different bone engaging members or texturing.

Figure 8:
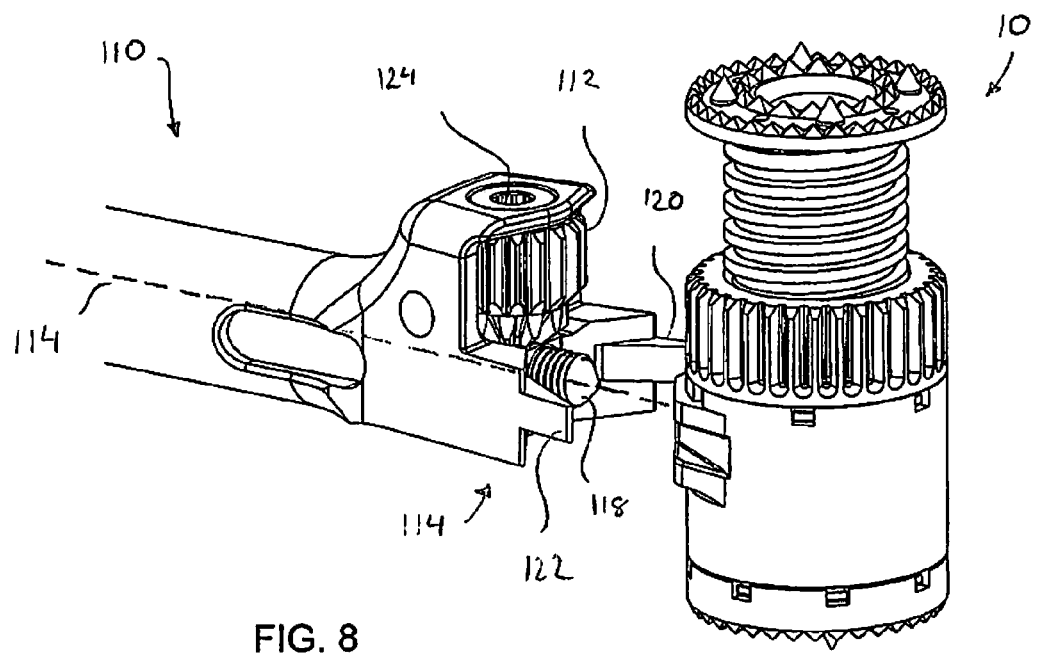
FIG. 8 is a perspective view of one embodiment of a tool according to the present invention.
Figure 9:
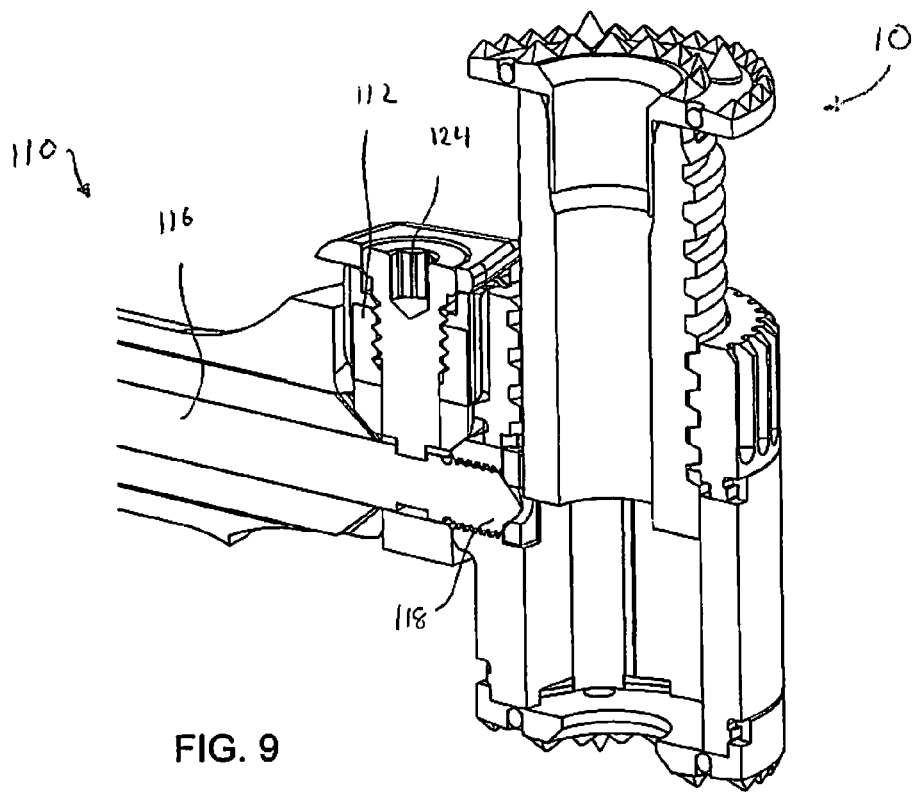
FIG. 9 is a cross-sectional view of the tool of FIG. 8 shown engaging an embodiment of an expandable implant according to the present invention.

Turning now to FIGS. 8-9, the implant 10 may be expanded by a tool 110 that includes a gear member 112 at its distal end 114. The tool 110 extends along a tool axis 114 and in operation the tool 110 is configured to engage the implant 10 such that the tool axis 114 is generally perpendicular to the longitudinal axis 18. The gear member 112 is configured to engage teeth 74 of the gear member 16 such that when the gear member 112 is rotated about the axis of the tool 110, the gear member 16 of the implant 10 is rotated about the longitudinal axis 18 and the inner member 12 translates along the longitudinal axis 18 to either expand or contract the implant 10. In a preferred embodiment, the tool 110 may include a central shaft 116 having a threaded distal tip portion 118 that extends distally beyond gear member 112 to facilitate location and mounting of tool 110 with the implant 10. The threaded distal tip portion 118 preferably includes a generally conical end portion and may be configured to extend radially through the opening 54 and threadably engage opening 54 in the outer member 14.

With continued reference to FIGS. 8-9, in one embodiment of prosthetic device 10 at least one, but preferably a plurality of mounting features or slots 52 are provided along the outer surface 48 of outer member 14. The tool 110 includes at least one, but preferably two, articulating arms 120, 122 that engage slots 52 for better engagement of the tool 110 with the implant 10 during insertion of the implant 10. In another preferred embodiment, the tool 110 may include arms 120, 122 that do not articulate.

In an exemplary use of the tool 110 with the implant 10, the tool 110 initially engages the slots 52 of the implant 10 via the arms 120, 122 and gear member 112 engages gear member 16 via their respective interdigitating teeth. A control member on the proximal end of the tool 110 (not shown) is manipulated to advance the central shaft 116 toward opening 54. The threaded tip portion 118 enters into opening 54 engaging the threads in opening 54 as well as engaging the through-hole 84 of locking member 80. It is also contemplated that the central shaft 116 is not movable with respect to the tool 110. In that embodiment, the entire tool 110 is moved so that the central shaft can enter and engage the opening 54 and the through-hole 84. As discussed earlier, the though-hole 84 is offset from opening 54, thus, when threaded tip 118 engages and advances into the opening 54 and the through-hole 84, the locking member 80 is pulled downwardly, riding along the conical edge of the tip 118 until the through-hole 84 is aligned with the opening 54. As the locking member 80 is pulled downwardly, the arms 82, 84 are flexed and the engagement member 90 disengages from the cutout 73 of the gear member 16 allowing the gear member 16 to rotate freely. The gear member 112 of tool 110 is then rotated via opening 114 which, in turn, rotates gear member 16. As discussed above, the rotation of gear member 16 results in the movement of inner member 12 causing the implant 10 to either expand or contract, depending on the direction the gear member 16 is rotated. Once the desired height for implant 10 is achieved, the tool member 110 is disengaged from implant 10. When the tool 110 is removed, the locking member 80 returns to the back to its initial position because of the arms 82, 84 returning back to their unflexed, at-rest state. The initial position of locking member 80 prevents the gear member 16 from turning because of the engagement of engagement member 90 with the cutouts 73. In that regard, implant 10 is locked from movement when the locking member 80 is in its initial position.

The benefit provided by the present locking mechanism is that it allows for a positive lock that engages and disengages automatically with the engagement and disengagement of the tool 110 with the implant 10, which minimizes the steps the surgeon must perform during the procedure.

Figure 10:
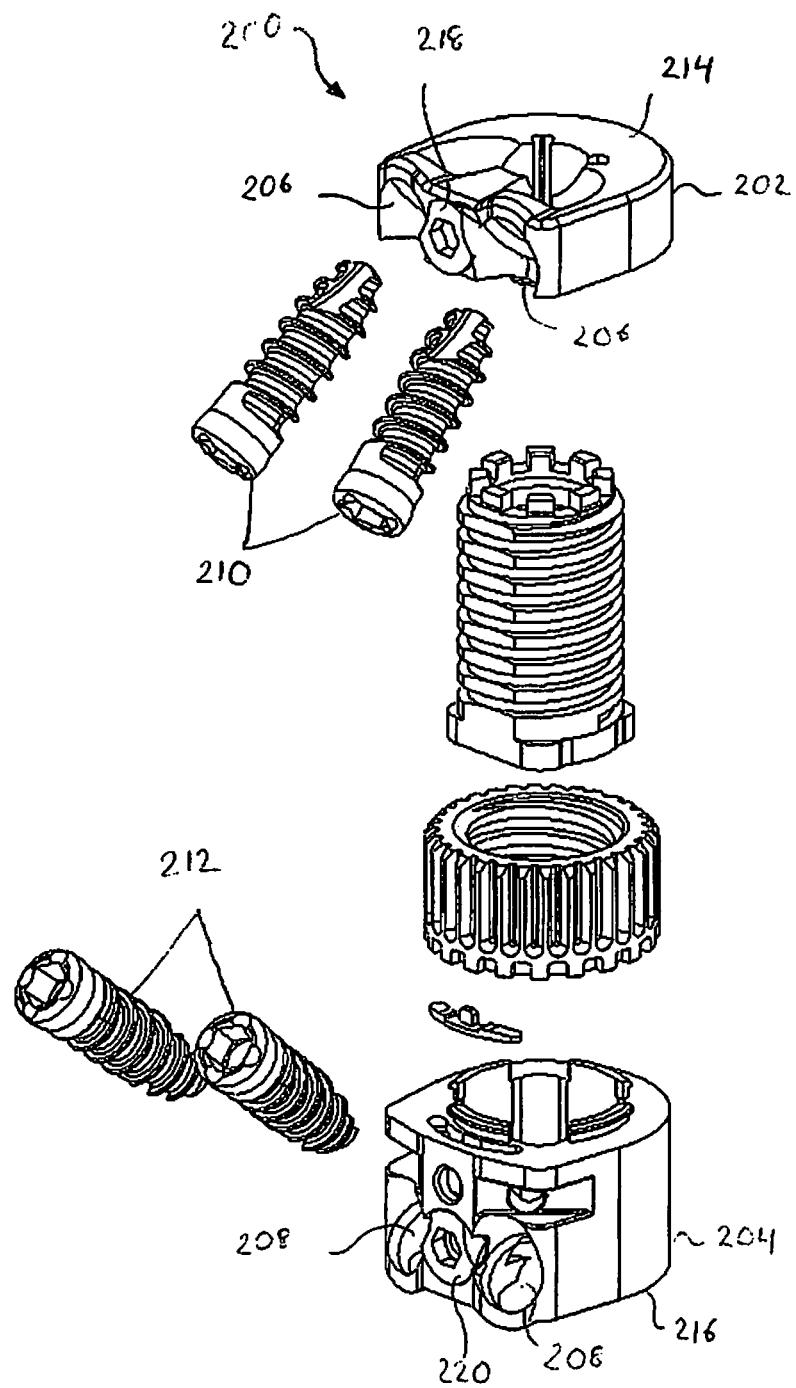
FIG. 10 is a perspective view of another embodiment of an implant according to the present invention.

Referring now to FIGS. 10-28, alternate preferred embodiments of endplates for the expandable implant 10 are shown. Looking at FIG. 10, in one variation, the endplates 202 and outer member 204 each include at least one screw hole 206, 208, but, preferably, each include two screw holes. The screw holes 206, 208 are configured and dimensioned to receive screws 210, 212. In a preferred embodiment, the screw holes 206, 208 are angled such that when the screws 210, 212 are seated in the screw holes 206, 208, the screws 210, 212 will extend outwardly from the superior surface 214 of endplate 202 and inferior surface 216 of outer member 204. Endplate 202 and outer member 204 also preferably include a locking element 218, 220 which, in a first position, allow the screws 210, 212 to back out from the seated position and, in a second position, block the screws 210, 212 from backing out of the seated position. In an exemplary use, once the implant 200 is installed and expanded to the desired position, the screws 210, 212 can be installed through the screw holes 206, 208 in such a manner as to purchase into the adjacent vertebral bodies. Once the screws 210, 212 are properly installed, including being engaged with the adjacent vertebral bodies, the locking elements 218, 220 can be actuated to block the screws 210, 212 from backing out of their installed position. The inclusion of screws 210, 212 in the endplate 202 and the outer member 204 provides for additional fixation of the implant 200 in the intervertebral space.

Figure 11:
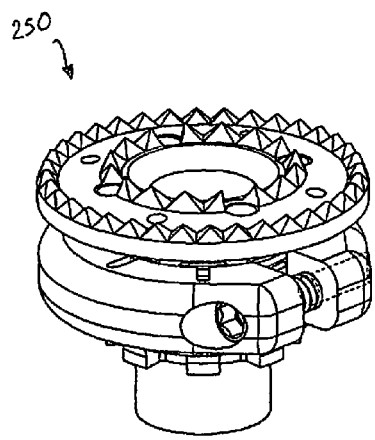
FIG. 11 is a perspective view of another embodiment of an endplate of an implant according to the present invention.
Figure 12:
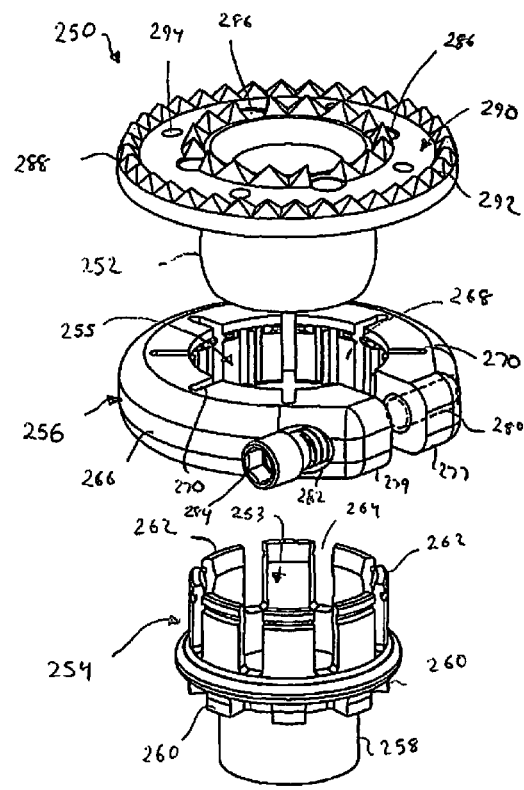
FIG. 12 is an exploded view of the endplate of FIG. 11.
Figure 13:
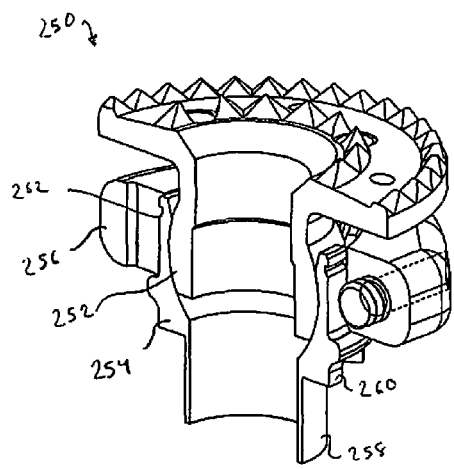
FIG. 13 is a cross-sectional view of the endplate of FIG. 11.

Turning to FIGS. 11-13, another preferred embodiment of an endplate 250 is shown. The endplate 250 is similar to endplate 20 but includes the additional functionality of being poly-axially rotatable with respect to an implant. In a preferred embodiment, endplate 250 includes a generally arcuate extension portion 252 which is received in an interior portion 253 of a receiving member 254 in such a manner as to allow the endplate 250 to move poly-axially with respect to the receiving member 254.

In a preferred embodiment, the receiving member 254 is received in an interior portion 255 of a locking ring 256. The receiving member 254 preferably includes a neck portion 258 as well as a plurality of tabs 260. The neck portion 258 is configured and dimensioned to be received within a hollow interior of an inner member, for example, in an interference or snap fit, and the plurality of tabs 260 interdigitate with tabs to connect and position the receiving member 254 with respect to an inner member. The receiving member 254 further includes a plurality of fingers 262 configured to cooperatively receive the extension portion 252 of endplate 250. A plurality of relief spaces or slots 264 are radially spaced between fingers 262 to allow fingers 262 to bend or flex radially.

In a preferred embodiment, the locking ring 256 has a generally annular, c-shape and includes an exterior wall 266, an interior wall 268, and ends 277, 279. The interior wall 268 preferably defines and interior portion 255. In a preferred embodiment, the interior wall 268 includes a plurality of channel 270 which are spaced radially along the locking ring 256. The channels 270 allow the locking ring 256 to bend or flex radially. The ends 277, 279 each include openings 280, 282 which may be partially threaded. A locking element 284 is configured and dimensioned to be threadingly received in the openings 280, 282. It also contemplated that that locking element 284 can engage the ends 277, 279 by other non-threaded means, such as a sliding fit.

With continued reference to FIGS. 11-13, in a preferred embodiment, the endplate 250 includes a plurality of mounting holes 286 spaced around the perimeter of the endplate 250 for receiving insertable bone engaging members. In one embodiment, bone engaging members, comprise conical spikes each having a cylindrical base portion configured to fit within holes 286, for instance, by press-fit or by threaded engagement. In alternate embodiments, differently shaped bone engaging members may be used, or in other embodiments no bone engaging members may be used. According to one preferred embodiment, endplate 250 has chamfered edges 288 around the perimeter to facilitate insertion and/or accommodate the shape of the vertebral bodies which they engage. The superior or bone engaging surfaces 290 of endplate 250 may also include numerous types of texturing to provide better initial stability and/or grasping contact between the end plate and the respective vertebrae. In a preferred embodiment, the texturing is a plurality of teeth 292. In preferred embodiments where the implant is manufactured from PEEK or other plastic materials, the endplate 250 may also include radio-opaque material, such as tantalum markers 294, which aid in providing location markers in radiographic images.

In an exemplary use, during the implant installation and expansion to the desired position, the endplate 250 can move in poly-axial fashion with respect to the implant to accommodate the anatomy of the adjacent vertebral body as well as accommodate the natural curvature of the spine, such as kyphosis and lordosis. More specifically, the arcuate extension portion 252 is free to move in the interior portion 253 of the receiving portion 254. The fingers 262 are generally compliant and can flex to accommodate the movement of the arcuate extension portion 252. Once the desired positioning of the endplate 250 is achieved, the endplate 250 can be locked in place. The endplate 250 is locked in place by actuating the locking element 284. As the element 284 engages the threading in opening 280,282 the ends 277, 279 of the locking ring 256 are brought closer together contracting the ring 254 and reducing the size of the interior portion 255. As the ring 254 contracts, the fingers 262 of the receiving member 254, abutting against the inner wall 268, are flexed radially inwardly pushing against the extension portion 252. As a result, the endplate 250 is locked in place.

Figure 14:
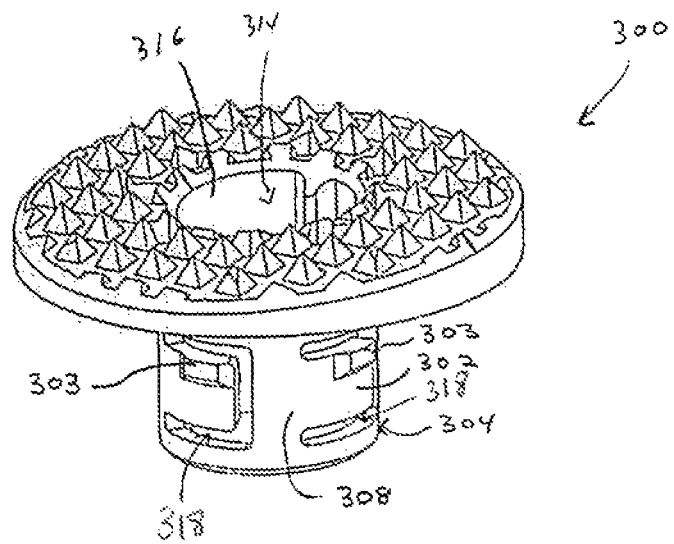
FIG. 14 is a perspective view of another embodiment of an endplate of an implant according to the present invention.
Figure 15:
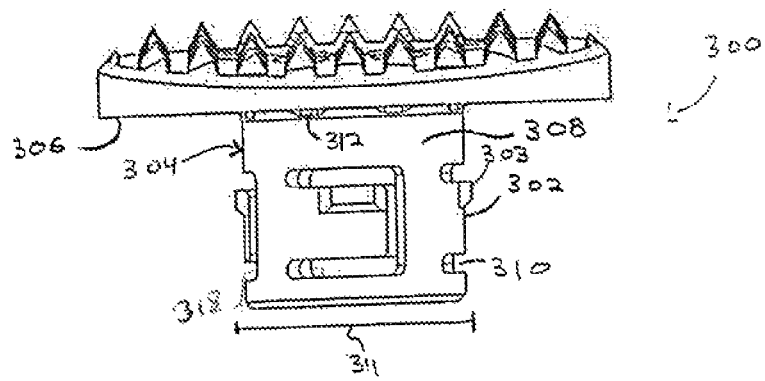
FIG. 15 is a side view of the endplate of FIG. 14.

Turning to FIGS. 14-15, another preferred embodiment of an endplate 300 is shown. The endplate is similar to the endplate 20 of FIGS. 1-3, but with the addition of flexible tabs 302 on the extension portion 304 for retaining the endplate 300 in the interior portion 404 of the inner member 400 (e.g., shown on FIGS. 18-20), As illustrated, the extension portion 304 extends downward from a lower surface 306 of the endplate 300. In a preferred embodiment, the extension portion 304 may have an exterior surface 308 in which the flexible tabs 302 are formed. As illustrated, the exterior surface 308 may have cutouts 310 around one or more sides of the flexible tabs 302. The cutouts 310 allow the flexible tabs 302 to bend or flex radially. The outermost external diameter 311 of the extension portion 304 with the flexible tabs 302 is sized to be slightly larger than the inner diameter of the interior portion 404 of the inner member. Accordingly, the flexible tabs 302 should flex radially inward as the extension portion 304 is inserted into the interior portion 404. In a preferred embodiment, the flexible tabs 302 include protrusions 303 that extend radially beyond the exterior surface 308 of the extension portion 304. The endplate 300 may also preferably include a hollow, interior portion 314 defined by interior surface 316. In a preferred embodiment, the interior surface 316 may include a protruding portion 318, which may extend longitudinally on the interior surface 316 as best seen in FIG. 14. The protruding portion 318 may be used as a visual reference to aid in assembly of the endplate 300 to the inner member 400. An instrument (not shown) may also engage the protruding portion 318 for mechanical and/or automatic alignment of the endplate 300 to the inner member 400 during assembly.

Endplate 300 may further include a plurality of tabs 312 which extend, for example, downward from the lower surface 306 of the endplate 300 that interdigitate with tabs 410 on the inner member 400 (e.g., shown on FIGS. 18-20) to prevent, for example, rotation of the endplate 300 with respect to the interior portion 404. In an alternative embodiment, instead of the tabs 312, a plurality of slots may be formed in the endplate 300 for receiving the tabs 410 on the interior portion 404. Where used, the slots can be cut through the endplate 300 or can be blind (made to a specified depth). In one embodiment, the endplate 300 may have eight slots. However, the endplate 300 may have more or less slots as desired for a particular application.

Figure 17:
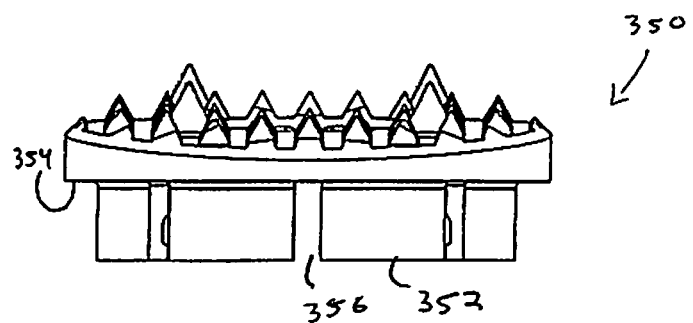
FIG. 17 is a side view of the endplate of FIG. 16.
Figure 16:
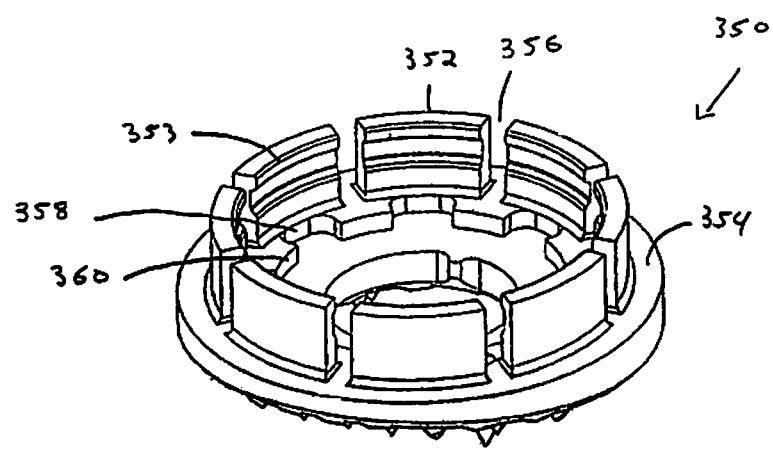
FIG. 16 is a perspective view of another embodiment of an endplate of an implant according to the present invention.

Turning to FIGS. 16-17, another preferred embodiment of an endplate 350 is shown. The endplate 350 is similar to the endplate 62 of FIGS. 1-3, but with the addition of flexible tabs 352 for retaining the endplate 350 on the proximal end 412 of the outer member 402 (e.g., shown on FIGS. 18-20). As illustrated, the flexible tabs 352 extend upward from an upper surface 354 of the endplate 350. In the illustrated embodiment, the endplate 350 includes eight flexible tabs 352. However, the endplate 350 may comprise more or less flexible tabs 352 as desired for a particular application. In a preferred embodiment, the flexible tabs 352 each include an upper lip 353. As illustrated, a plurality of slots or relief spaces 356 are radially spaced between the flexible tabs 352 to allow the flexible tabs 352 to bend or flex radially. The inner diameter of a cylinder formed by the flexible tabs 352 is sized to be slightly smaller than an external diameter of the proximal end 412 of the outer member 402 (e.g., shown on FIG. 20). Accordingly, the flexible tabs 352 should flex radially outwards as the flexible tables 352 are inserted onto the proximal end 412. In a preferred embodiment, the endplate 350 has an inner surface 358 that includes a plurality of tabs 360 spaced radially around the inner surface 358. The tabs 360 interdigitate with tabs 418 on the outer member 402 (e.g., shown on FIGS. 18-20) to prevent, for example, rotation of the endplate 350 with respect to the outer member 402.

Figure 20:
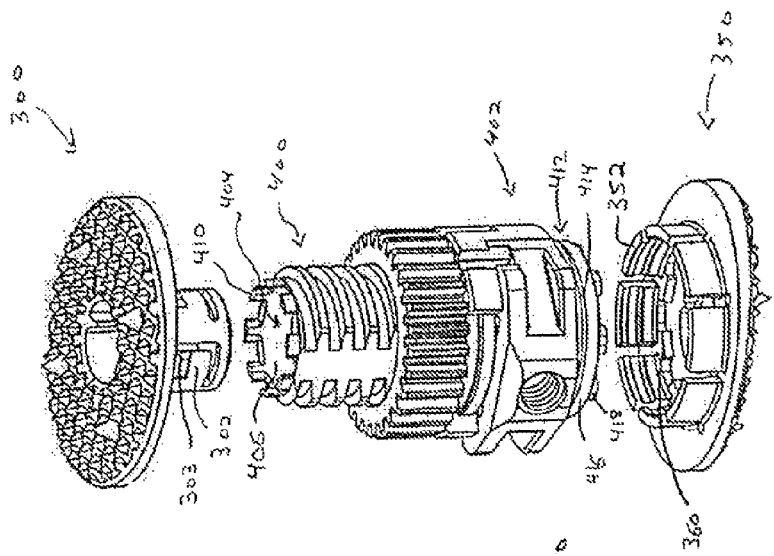
FIG. 20 is an exploded view of the implant of FIG. 18.
Figure 19:
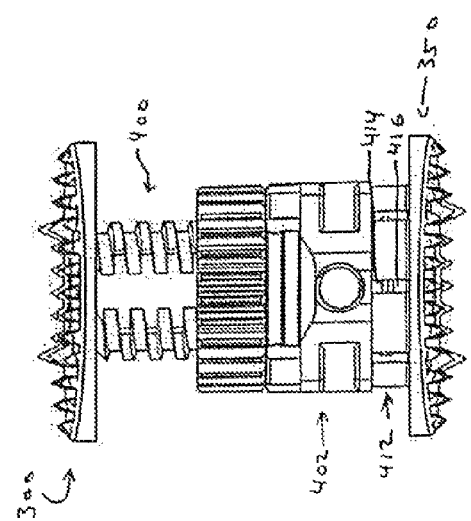
FIG. 19 is a side view of the implant of FIG. 18.
Figure 18:
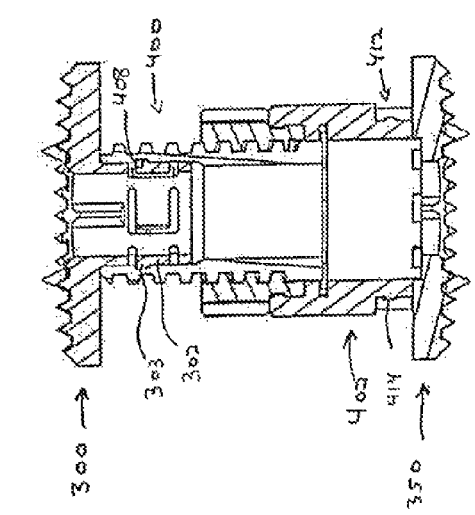
FIG. 18 is a cross-sectional view of another embodiment of an implant shown with the endplates of FIGS. 14-17 according to the present invention.

As seen in FIGS. 18-20, the endplates 300, 350 are shown wherein the endplate 300 connects to inner member 400 and the endplate 350 connects to outer member 402. In a preferred embodiment, the extension portion 304 of the endplate 300 is introduced into an interior portion 404 of the inner member 400. As the extension portion 304 is introduced, the protrusions 303 of the flexible tabs 302 on the extension portion 304 engage the inner surface 406 of the inner member 400 causing the flexible tabs 302 to flex radially inwardly. This reduces the size of the extension portion 304, allowing the extension portion 304 to be placed into the interior portion 404 of the inner member 400. In a preferred embodiment, the interior surface 406 of the inner member 400 has a cutout feature 408 in the interior surface 406, as best seen in FIG. 18. In one embodiment, the cutout feature 408 is a cylindrical cutout that extends around the interior surface 406. When the protrusions 303 are aligned with the cutout feature 408, the flexible tabs 302 should flex radially outward such that the protrusions 303 are cooperatively received within the cutout feature 408. In this regard, the endplate 300 is retained from longitudinal and lateral movement. As shown in FIG. 20, the inner member 400 may also include a plurality of tabs 410 that interdigitate with tabs 312 on the endplate 300 (e.g., shown on FIG. 15) for preventing rotational movement of the endplate 300 with respect to the inner member 400.

In a preferred embodiment, the endplate 350 can be placed onto a proximal end 412 of the outer member 402. As the endplate 350 is placed onto the proximal end 412, the flexible tabs 352 engage the proximal end 412 causing the flexible tabs 352 to flex radially outward. This increases the size of the cylinder formed by the flexible tabs 352, allowing the endplate 350 to be placed onto the outer member 402. In a preferred embodiment, the proximal end 412 of the outer member 402 includes a protuberance 414 that engages the flexible tabs 352 causing the flexible tabs 352 to flex radially outwardly. In one embodiment, the protuberance 414 extends radially around an outer surface 416 of the proximal end 412. When the upper lips 353 of the flexible tabs 352 have passed the protuberance 414, the flexible tab 352 should flex radially inward such that the upper lips 353 of the flexible tabs 352 cooperatively engage the protuberance 414 of the proximal end 412. In this regard, the endplate 300 is retained from longitudinal and lateral movement. As shown in FIG. 20, the outer member 402 may also include a plurality of tabs 414 that interdigitate with tabs 360 on the endplate 350 for preventing rotational movement of the endplate 350 with respect to the outer member 402.

Figures 21, 22:
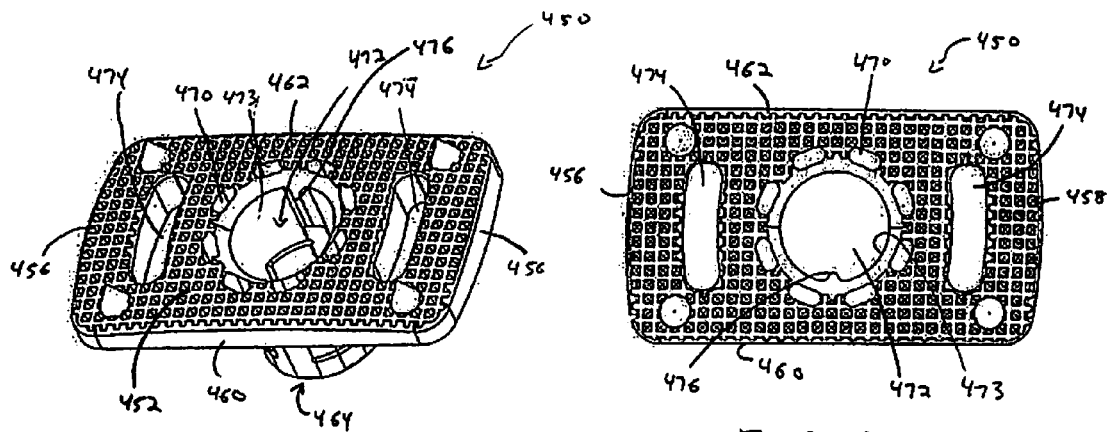
FIG. 21 is a perspective view of another embodiment of an endplate of an implant according to the present invention.
FIG. 22 is an end view of the endplate of FIG. 21.
Figure 23:
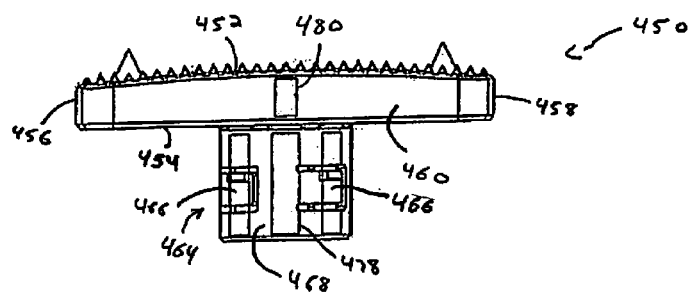
FIG. 23 is a side view of the implant of FIG. 21.

Turning to FIGS. 21-23, another preferred embodiment of an endplate 450 is shown. The endplate 450 is similar to the endplate 300 of FIGS. 14-15 except that the endplate 450 is generally rectangular in shape. As illustrated, the endplate 450 may have an upper bone engaging surface 452 and a lower surface 454. The endplate 450 also may have a first end 456, a second end 458, a first lateral side 460, and a second lateral side 462. In a preferred embodiment, the first and second lateral sides 460, 462 each have a gradual increase in height moving away from the first and second ends 456, 458 with the highest portion of the sides 460, 462 being in the mid portion, as best seen in FIG. 23. The endplate 450 may also have a hollow interior portion 472 defined by an interior surface 473. In one embodiment, the interior portion 472 may be a through bore that extends through the endplate 450.

As illustrated, an extension portion 464 extends downwardly from the lower surface 454 of the endplate 450. Flexible tabs 466 may be formed in an exterior surface 468 of the extension portion 464 for securing the endplate 450 to the inner member 400 (e.g., shown on FIG. 20). In a preferred embodiment, the endplate 450 further includes a plurality of slots 470 in the lower surface 454 for receiving corresponding tabs 410 on the inner member 400 (e.g., shown on FIG. 20). As illustrated, the slots 470 may be spaced around interior portion 472 of the endplate 450.

In a preferred embodiment, the endplate 450 further includes one or more slots 474 that extend from the upper bone engaging surface 452 through the lower surface 454. In the illustrated embodiment, two slots 474 are shown. The slots 474 may be sized to receive bone growth or similar bone growth inducing material and/or allow increased blood supply to any such material placed below the lower surface 454 of the endplate 450.

With continued reference to FIGS. 21-23, the endplate 450 may further include one or more features for aiding assembly of the endplate 450 onto the inner member 400 (e.g., shown on FIG. 20). For example, the interior surface 473 of the interior portion 472 may include a protruding portion 476. The protruding portion 476 may be used as a visual indicator to aid in assembly of the endplate 450 to the inner member 400. An instrument (not shown) may also engage the protruding portion 476 for mechanical and/or automatic alignment of the endplate to the inner member 400 during assembly. By way of further example, one or more visual indicators 478 may be disposed in the exterior surface 468 of the extension portion 464 to provide a visual indication of when the endplate 450 is aligned with the inner member 400, such as when the slots 470 in the endplate 450 are aligned with the tabs 410 in the inner member 400. In one embodiment, the visual indicators 478 may be in the form of etched lines or blocks on the exterior surface 468. By way of further example, one or more visual indicators 480 may be disposed on the first lateral side 460 of the endplate to provide a visual indication of when the endplate 450 is aligned with the inner member 400. As illustrated, the visual indicators 480 in the first lateral side 460 may be in the form of etched lines or blocks. The visual indicators 480 are not limited to the first lateral side 460 but may be placed on any either of the ends 456, 458 and/or lateral sides 460, 462 of the endplate 450.

Figure 24:
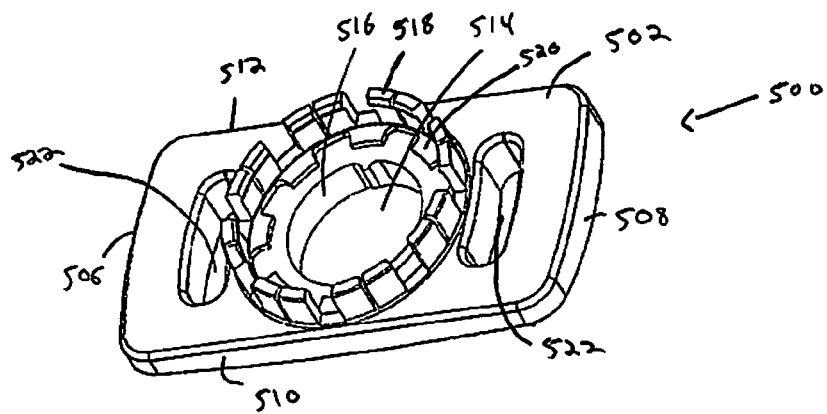
FIG. 24 is a perspective view of another embodiment of an endplate of an implant according to the present invention.
Figure 25:
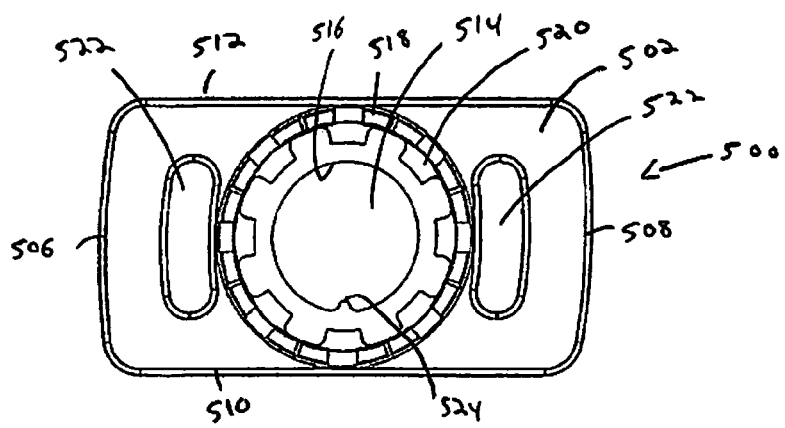
FIG. 25 is an end view of the endplate of FIG. 24.
Figure 26:
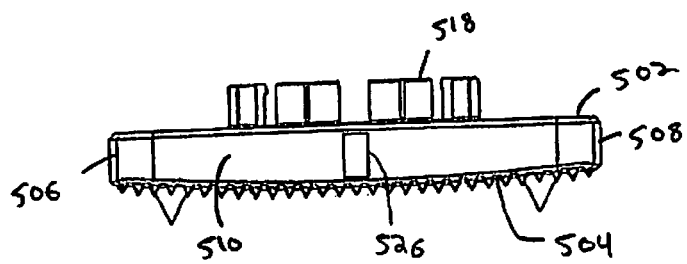
FIG. 26 is a side view of the endplate of FIG. 24.

Turning to FIGS. 24-26, another preferred embodiment of an endplate 500 is shown. The endplate 500 is similar to the endplate 350 of FIGS. 16-17 except that the endplate 500 is generally rectangular in shape. The endplate 500 may have an upper surface 502 and a lower bone engaging surface 504. The endplate 500 also may have a first end 506, a second end 508, a first lateral side 510, and a second lateral side 512. In a preferred embodiment, the first and second lateral sides 510, 512 each have a gradual increase in height moving away from the first and second ends 506, 508 with the highest portion of the sides 510, 512 being in the mid portion, as best seen in FIG. 26. The endplate 500 may also have a hollow interior portion 514 defined by an interior surface 516. In one embodiment, the interior portion 514 may be a through bore that extends through the endplate 500. As illustrated, flexible tabs 518 extend upward from the upper surface 502 of the endplate 500 for securing the endplate 500 on the outer member 402 (e.g., shown on FIG. 20). The endplate 500 further may a plurality of tabs 520 spaced radially around the inner surface 516 for receiving corresponding tabs 418 in the outer member 402 (e.g., shown on FIG. 20). In a preferred embodiment, the endplate 500 further includes one or more slots 522 that extend from the lower bone engaging surface 504 through the upper surface 502. In the illustrated embodiment, two slots 522 are shown. The slots 522 may be sized to receive bone growth or similar bone growth inducing material and/or allow increased blood supply to any such material placed above the upper surface 502 of the endplate 500.

With continued reference to FIGS. 24-26, the endplate 500 may further include one or more features for aiding assembly of the endplate 500 onto the outer member 402 (e.g., shown on FIG. 20). For example, the inner surface 516 of the interior portion may include a protruding portion 524. The protruding portion 524 may be used as a visual indicator to aid in assembly of the endplate 500 to the outer member 402. An instrument (not shown) may also engage the protruding portion 524 for mechanical and/or automatic alignment of the endplate to the member during assembly. By way of further example, one or more visual indicators 526 may be disposed on the first lateral side 510 of the endplate 510 to provide a visual indication of when the endplate 500 is aligned with the outer member 402. As illustrated, the visual indicators 526 in the first lateral side 510 may be in the form of etched lines or blocks. The visual indicators 526 are not limited to the first lateral side 510 but may be placed on either of the ends 506, 508 and/or lateral sides 510, 512 of the endplate 500.

Figure 27:
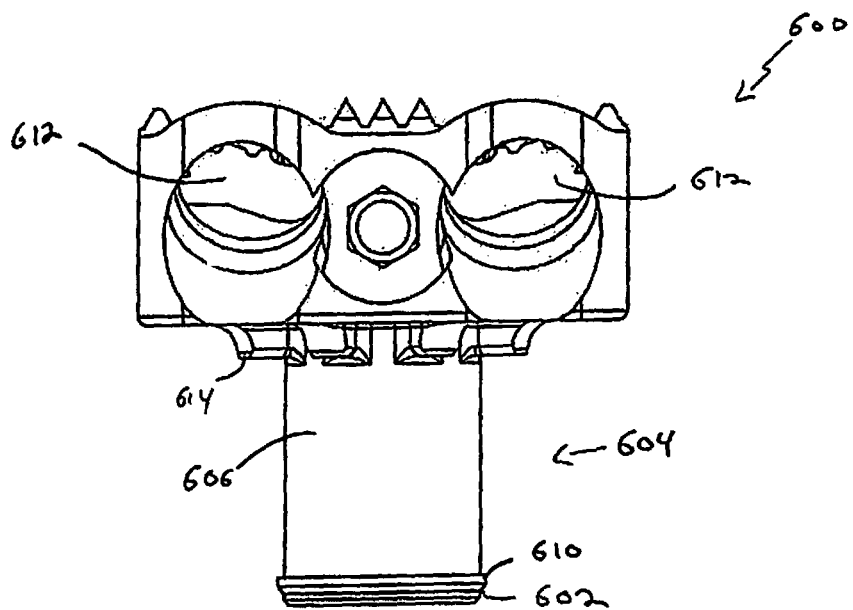
FIG. 27 is a side view of another embodiment of an endplate of an implant according to the present invention.
Figure 28:
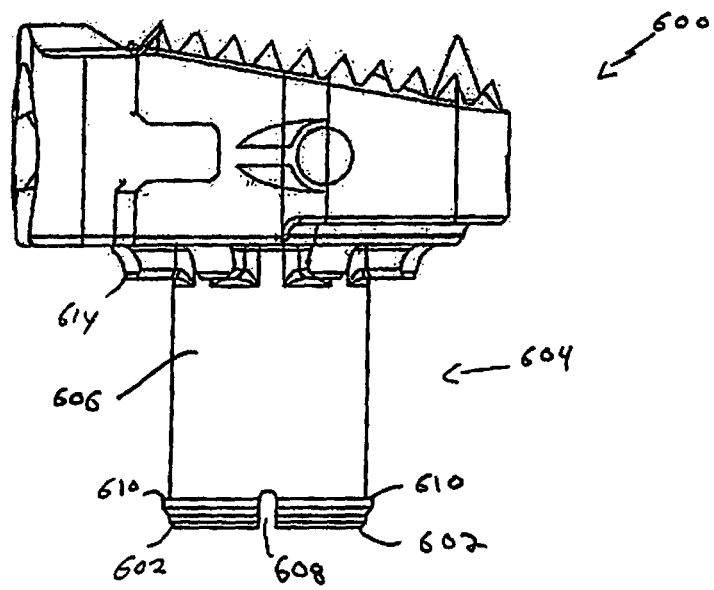
FIG. 28 is a side view of the endplate of FIG. 27 shown rotated 90° with respect to the view of FIG. 27.

Turning to FIGS. 27-28, another preferred embodiment of an endplate 600 is shown. The endplate 600 is similar to the endplate 300 of FIGS. 14-15, except that the endplate 600 includes only two flexible tabs 602 on the extension portion 604. As previously discussed, the flexible tabs 602 are configured to retain the extension portion 604 in the interior portion 664 of the inner member 650 (e.g., shown on FIGS. 29-30). In a preferred embodiment, the extension portion 604 may have an exterior surface 606. The extension portion 604 may have cutouts 608 in the exterior surface 606 between the flexible tabs 602 to allow the flexible tabs 602 to bend or flex radially. Accordingly, the flexible tabs 602 should bend or flex radially inward as the extension portion 604 is inserted into the interior portion 664 of the inner member 650. As illustrated, the cutouts 608 may be in the form of one or more longitudinally extending slots. In a preferred embodiment, the flexible tabs 602 also include protrusions 610 that extend radially from the beyond the exterior surface 606. As best seen in FIG. 27, the endplate 600 further may comprise one or more screw holes 612 and preferably at least two. The screw holes 612 are configured and dimensioned to receive screws (not shown). In an exemplary use, the screws can be installed through the screw holes 612 in such a manner as to purchase the adjacent vertebral body.

Figure 30:
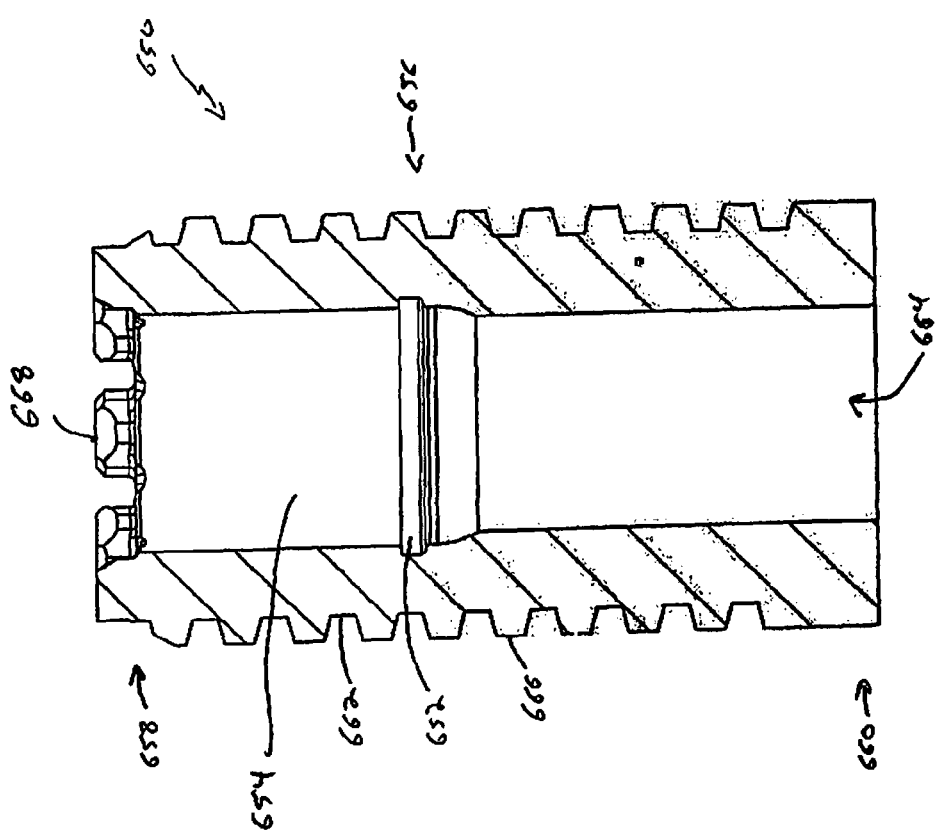
FIG. 30 is a cross-sectional view of the inner member of FIG. 29.
Figure 29:
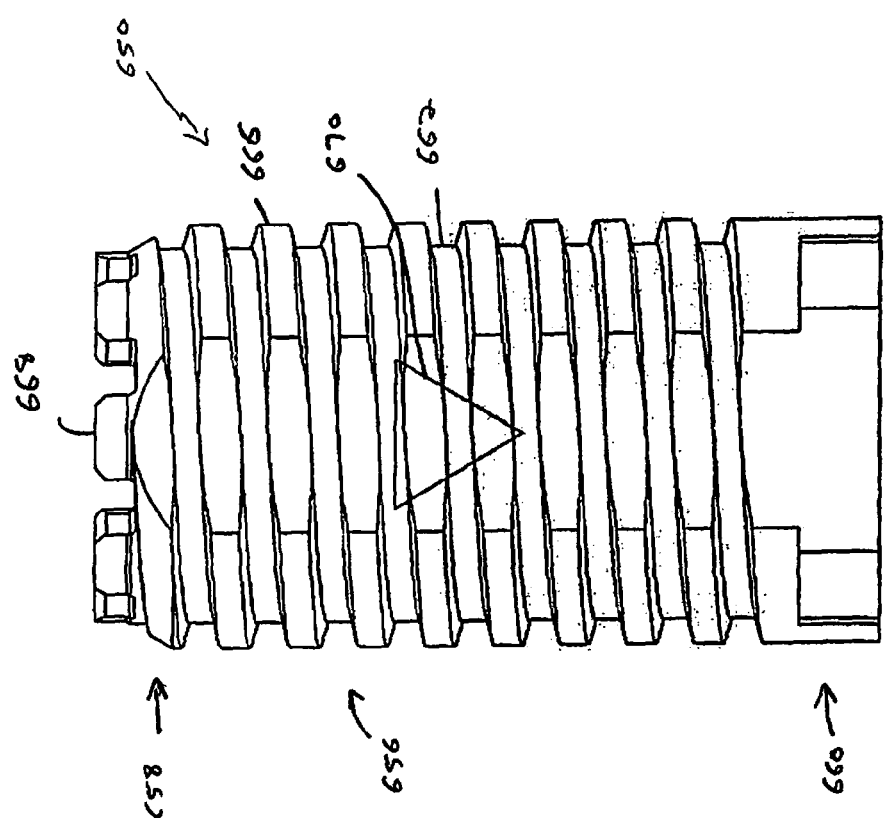
FIG. 29 is a side view of an inner member of an implant according to the present invention.

Referring now to FIGS. 29-30, an alternate preferred embodiment of an inner member 650 is shown. The inner member 650 is similar to the inner member 12 shown on FIGS. 1-4, except that the inner member 650 includes a cutout feature 652 in an inner surface 654 for retaining the flexible tabs 602 of the extension portion 604 (e.g., shown on FIGS. 27-28). In a preferred embodiment, the inner member 650 has a generally cylindrical body 656 with a distal end 658 and a proximal end 660. As illustrated, the body 656 of the inner member 650 may comprise an inner surface 654 and an outer surface 662 and generally defines a hollow interior portion 664 extending axially therethrough. The inner surface 654 at least partially surrounds the hollow interior portion 664. At least part of the outer surface 662 includes external threads 666. In one embodiment, the cutout feature 408 extends around the interior surface 406. Located proximate the distal end 658 of the body 656 are a plurality of tabs 668 which assist in connecting and positionally locating the endplate 600 (e.g., shown on FIGS. 27-28). In a preferred embodiment, the body 656 is configured and dimensioned to be cooperatively received within outer member 702 (e.g., shown on FIG. 33).

Figure 33:
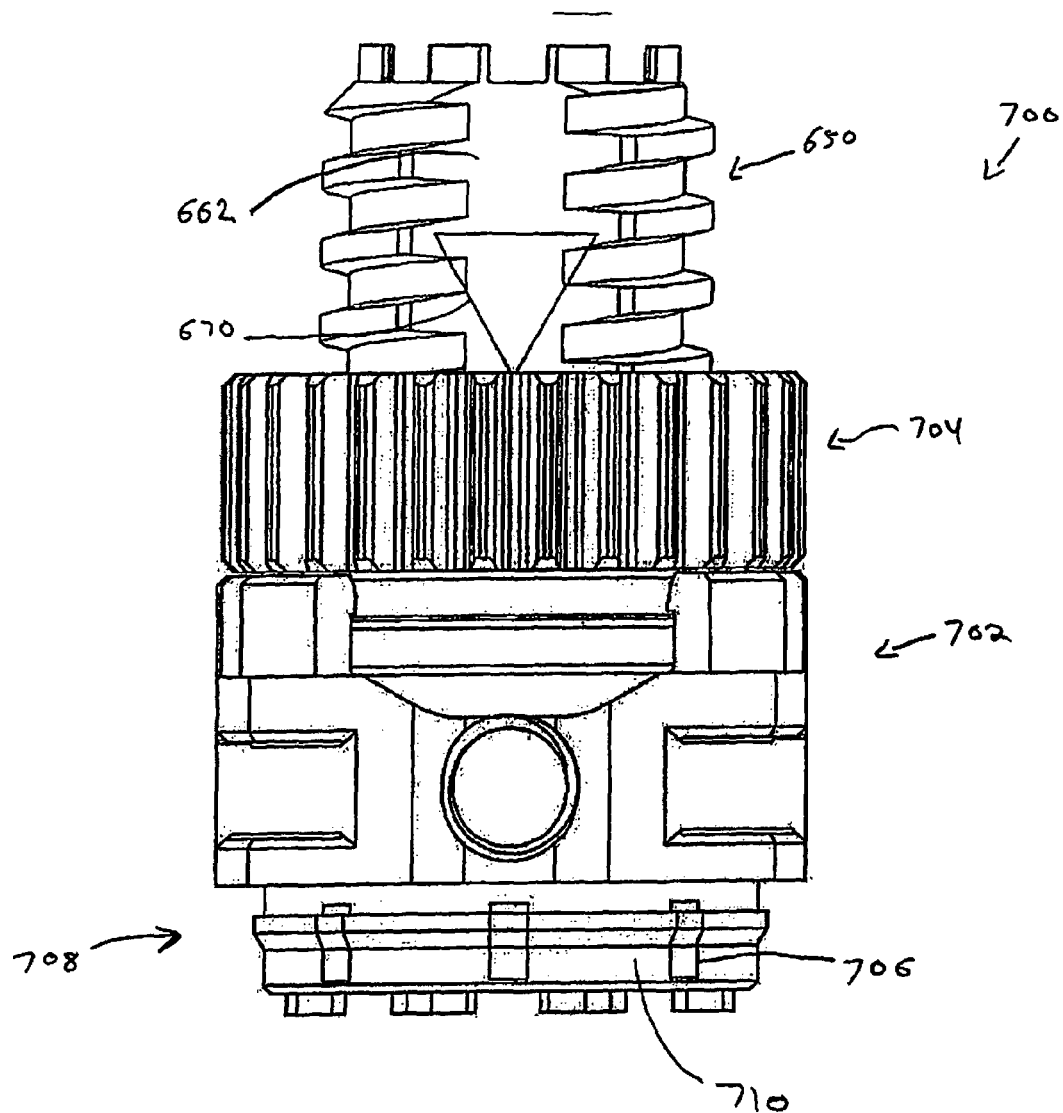
FIG. 33 is a side view showing another embodiment of an implant according to the present invention.

In a preferred embodiment, the inner member 650 may further include one or more features for aiding a user in expansion of an implant 700 (e.g., shown on FIG. 33). For example, the outer surface 662 of the body 656 may include one or more visual indicators 670 to provide a visual indication of when the implant is at a desired level of expansion, for example, at its maximum level of expansion. The visual indicator 670 could be disposed on the outer surface 662 at a location just above the gear member 704 when the implant 700 is fully expanded. As illustrated, the visual indicator 670 is in the form of triangle etched into the outer surface 662 of the body 656, However, it should be appreciate that other lines, shape, numbers, or words, for example, could be used to provide the visual indication on the outer surface 662

Figure 32:
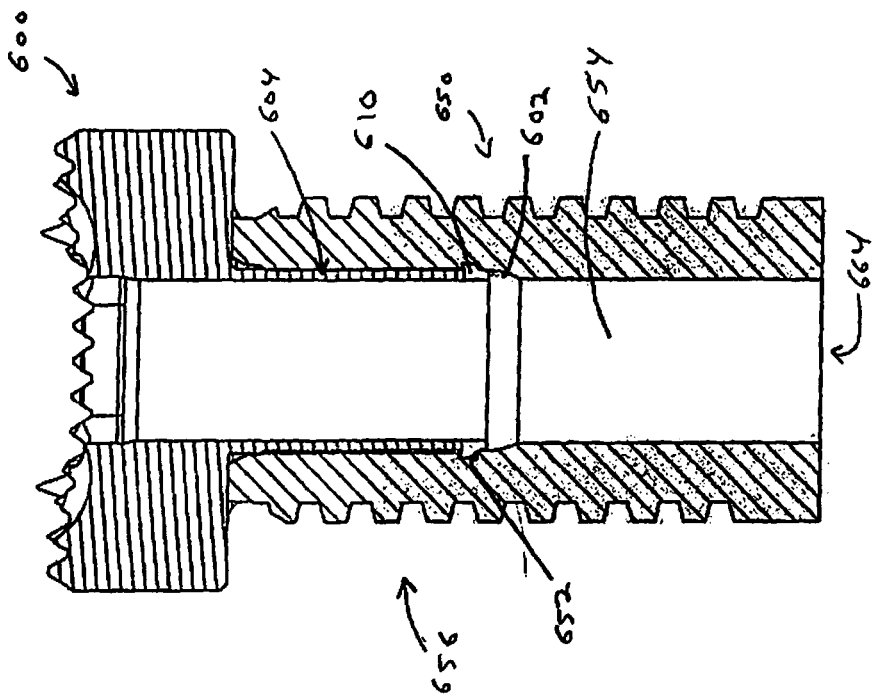
FIG. 32 is a cross-section view showing the endplate of FIG. 27 received in the inner member of FIG. 29.
Figure 31:
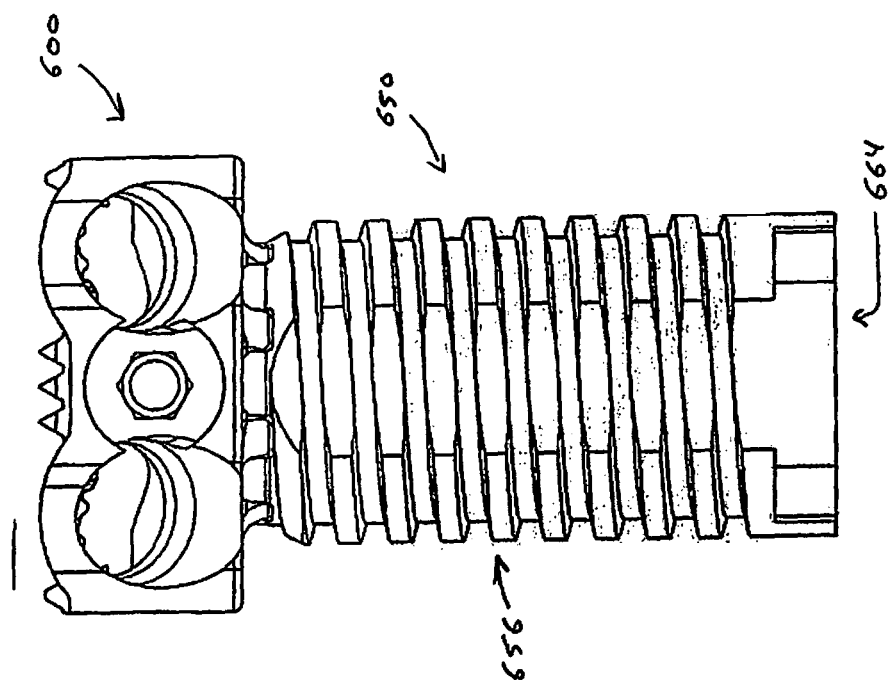
FIG. 31 is a side view showing the endplate of FIG. 27 received in the inner member of FIG. 29.

Turning now to FIGS. 31-32, the endplate 600 and inner member 650 are shown wherein the endplate 600 connects to the inner member 650. In a preferred embodiment, the extension portion 604 of the endplate 600 is introduced into an interior portion 664 of the body 656 of the inner member 600. As the extension portion 604 is introduced, the protrusions 610 of the flexible tabs 602 on extension portion 604 engage the inner surface 654 of the body 656 of the inner member 650 causing the flexible tabs 602 to flex radially inwardly. This reduces the size of the extension portion 604, allowing the extension portion 604 to be placed into the interior portion 664 of the body 656 of the inner member 650. When the protrusions 610 are aligned with the cutout feature 652, the flexible tabs 602 should flex radially outward such that the protrusions 610 are cooperatively received within the cutout feature 652. In this regard, the endplate 600 is retained from longitudinal and lateral movement. The inner member 400 may also include a plurality of tabs 668 (e.g., shown on FIGS. 29-30) that interdigitate with tabs 614 on the endplate 600 (e.g., shown on FIGS. 27-28) for preventing rotational movement of the endplate 600 with respect to the inner member 650.

Referring now to FIG. 33, an alternate preferred embodiment of an implant 700 is shown. The implant 700 preferably comprises an inner member 650 which may be telescopically received within an outer member 702. The implant 700 further comprises a gear member 704 generally configured to effect translation of the inner member 650 with respect to the outer member 702 thereby allowing for expansion and contraction of the implant 700. While not shown, one or more endplates may be coupled to the inner member 650 and the outer member 702, respectively.

As shown by FIG. 33, the implant 700 is at its maximum level of expansion. The inner member 650 includes at least one visual indicator 670 on its outer surface 662 to provide a visual indication that the implant 700 is fully expanded, for example. In the illustrated embodiment, the visual indicator 670 is shown just above the gear member 704 indicating that the implant 700 is at its maximum level of expansion.

In a preferred embodiment, the outer member 702 may include one or more features for aiding assembly of an endplate onto the outer member 702. For example, one or more visual indicators 706 may be positioned at a proximal end 708 of the outer member 702. In the illustrated embodiment, the visual indicators 706 may be positioned around an outer surface 710 of the proximal end 708. The visual indicators 706 preferably may provide a visual indication of when the tabs on the endplate are properly aligned with the outer member 702. As illustrated, the visual indicators 706 may be in the form of lines or blocks etched into the outer surface 710.

While the invention herein disclosed has been described by means of specific embodiments and applications thereof, numerous modifications and variations can be made thereto by those skilled in the art without departing from the scope of the invention as set forth in the claims. Although individual embodiments are discussed herein, the invention covers all combinations of all those embodiments.

What is claimed is:

1. An expandable prosthetic implant for engagement between vertebrae, comprising:
    an inner member having a hollow interior portion and a threaded external portion, wherein the inner member comprises an interior surface at least partially surrounding the hollow interior portion, wherein the interior surface has a cylindrical cutout extending around the interior surface;
    a first endplate configured to engage a first vertebral body, wherein the first endplate comprises an extension portion configured to be received within the hollow interior portion of the inner member, wherein the extension portion comprises flexible tabs configured to secure the first endplate to the inner member;
    an outer member having an opening and a hollow interior portion configured to coaxially receive the inner member therein, wherein the inner and outer members are moveable relative to each other along a longitudinal axis;

a second endplate configured to engage a second vertebral body, wherein the second endplate comprises flexible tabs extending from a surface of the second endplate, the flexible tabs configured to secure the second endplate to the outer member;

a gear member positioned coaxial to the inner member and outer member and axially fixed to the outer member and freely rotatable with respect to the outer member;

a locking member received in the outer member, the locking member having at least one arm, an engagement member, and a through-hole, wherein the gear member threadedly engages the threaded portion of the inner member, wherein the gear member comprises a plurality of cutouts capable of being engaged by the engagement member, and wherein one or more protrusions on the flexible tabs of the first endplate are received in the cylindrical cutout of the inner member preventing the first endplate from longitudinal movement wherein in a first position, the engagement member of the locking member is received in the cutout of the gear member preventing the gear member from rotating and in a second position, the engagement member of the locking member is not received in the cutout of the gear member allowing the gear member to rotate, wherein in the first position, the through-hole of the locking member has a central axis that is offset from a central axis of the opening in the outer member and in the second position, the through-hole of the locking member is coaxial with the opening in the outer member.

2. The implant of claim 1, wherein in the first position, the at least one arm is not flexed, and in the second position, the at least one arm is flexed.

3. An expandable prosthetic implant for engagement between vertebrae, comprising:

an inner member having a hollow interior portion and a threaded external portion, wherein the inner member comprises an interior surface at least partially surrounding the hollow interior portion, wherein the interior surface has a cutout;

a first endplate configured to engage a first vertebral body, wherein the first endplate comprises an extension portion configured to be received within the hollow interior portion of the inner member, wherein the extension portion comprises flexible tabs configured to secure the first endplate to the inner member;

an outer member having a hollow interior portion configured to coaxially receive the inner member therein, wherein the inner and outer members are moveable relative to each other along a longitudinal axis;

a second endplate configured to engage a second vertebral body, wherein the second endplate comprises flexible tabs extending from a surface of the second endplate, the flexible tabs configured to secure the second endplate to the outer member;

a gear member positioned coaxial to the inner member and outer member and axially fixed to the outer member and freely rotatable with respect to the outer member, wherein the gear member threadedly engages the threaded portion of the inner member, wherein the implant is configured to engage the vertebrae such that first and second endplates are oriented in a predetermined alignment with respect to the first and second vertebral bodies, and wherein the gear member comprises gear teeth extending around the perimeter of the gear member, the gear teeth extending substantially from a proximal end of the gear member to a distal end of the gear member wherein in a first position, an engagement member of a locking element is received in the cutout of the gear member preventing the gear member from rotating and in a second position, the engagement member of the locking element is not received in the cutout of the gear member allowing the gear member to rotate, wherein in the first position, a through-hole of the locking element has a central axis that is offset from a central axis of an opening in the outer member and in the second position, the through-hole of the locking member is coaxial with the opening in the outer member.

4. The implant of claim 3, wherein the implant has a longitudinal axis and the gear teeth extend substantially parallel to the longitudinal axis.

5. The implant of claim 3, wherein the gear teeth are exposed and configured to be accessible by a tool member, the tool member engages the gear teeth substantially parallel to the longitudinal axis.

6. The implant of claim 3, wherein the inner member, outer member, and gear member are made of a PEEK plastic material.

7. The implant of claim 3, wherein the locking element affixes the inner member with respect to the outer member.

8. The implant of claim 3, wherein the inner member is rotationally fixed with respect to the outer member.

9. The implant of claim 8, wherein the inner member comprises a flattened portion and the outer member comprises a flattened portion, the flattened portions cooperate to prevent rotational movement of the inner member with respect to the outer member.

10. The implant of claim 8, wherein the inner member comprises a base portion having at least one lobe and the outer member comprises at least one depression, the lobes and depressions cooperate to prevent rotational movement of the inner member with respect to the outer member.

11. The implant of claim 3, wherein the first endplate and the second endplate each comprise at least one screw hole for receiving a screw.

12. The implant of claim 3, wherein the first and second endplates each include at least one bone engaging member extending longitudinally from the first and second endplates.

13. The implant of claim 3, wherein the flexible tabs on the first endplate engage the cutout on the interior surface of the inner member.

14. The implant of claim 3, wherein the flexible tabs on the first endplate are formed by cutouts in an exterior surface of the extension portion.

15. The implant of claim 3, wherein the flexible tabs on the second endplate engage a cutout on one end of the outer member.

16. The implant of claim 3, wherein the first endplate comprises a plurality of tabs or slots configured to engage a plurality of tabs extending from one end of the inner member to restrict rotation of the first endplate with respect to the inner member, and wherein the second endplate comprises a plurality of tabs spaced radially around an inner surface of the second endplate, the plurality of tabs in the second endplate configured to engage a plurality of tabs extending from one end of the outer member to restrict rotation of the second endplate with respect to the outer member.

17. The implant of claim 3, wherein one or more visual indicators are formed on one or more surfaces of the first endplate for providing a visual indication of alignment of the first endplate with the inner member, and wherein one or more visual indicators are formed on one or more surfaces of the second endplate for providing a visual indication of alignment of the second endplate with the outer member.

18. The implant of claim 3, wherein one or more visual indicators are formed on an outer surface of the inner member for providing a visual indication of expansion of the implant.

* * * * *